United States Patent
Mitsui et al.

(10) Patent No.: US 10,342,420 B2
(45) Date of Patent: Jul. 9, 2019

(54) ENDOSCOPE ACCESSORY CASE

(71) Applicant: OLYMPUS CORPORATION, Tokyo (JP)

(72) Inventors: Yohei Mitsui, Hachioji (JP); Shinichiro Kawachi, Inagi (JP); Hisato Kogure, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 124 days.

(21) Appl. No.: 15/636,707

(22) Filed: Jun. 29, 2017

(65) Prior Publication Data

US 2017/0296045 A1    Oct. 19, 2017

Related U.S. Application Data

(63) Continuation of application No. PCT/JP2016/075220, filed on Aug. 29, 2016.

(30) Foreign Application Priority Data

Mar. 29, 2016   (JP) .................................. 2016-065771

(51) Int. Cl.
*A61B 50/39*    (2016.01)
*A61B 90/70*    (2016.01)
(Continued)

(52) U.S. Cl.
CPC .............. *A61B 1/121* (2013.01); *A61B 1/123* (2013.01); *A61B 50/39* (2016.02); *A61B 90/70* (2016.02);
(Continued)

(58) Field of Classification Search
USPC .................................. 206/439; 220/255, 580
See application file for complete search history.

(56) References Cited

U.S. PATENT DOCUMENTS

5,072,849 A  *  12/1991  Blau ................... B65D 47/265
                                                  220/253
2007/0193605 A1    8/2007  Kuroshima et al.
2013/0146108 A1    6/2013  Suzuki et al.

FOREIGN PATENT DOCUMENTS

EP    1815782 A2    8/2007
EP    2641532 A1    9/2013
(Continued)

OTHER PUBLICATIONS

Japanese Office Action dated Mar. 7, 2017 issued in JP 2016-571773.

*Primary Examiner* — Kevin Joyner
(74) *Attorney, Agent, or Firm* — Scully, Scott, Murphy & Presser, P.C.

(57) ABSTRACT

An endoscope accessory case includes: a case body made up of a bottom portion and an impermeable trunk portion, the case body including an opening portion provided in a top face, and a fluid introduction port configured to introduce a fluid; and an impermeable lid, the lid including a contact portion configured to come into contact with the case body, and a bubble lead-out edge located at a position apart from an inner circumference of the case body and configured to lead out bubbles separated from endoscope accessories when the endoscope accessories held in the case body are agitated by being pushed by the fluid, the lid being configured to detachably cover the opening portion.

5 Claims, 7 Drawing Sheets

(51) Int. Cl.
*A61B 1/12* (2006.01)
*A61B 50/31* (2016.01)
(52) U.S. Cl.
CPC ......... *A61B 50/31* (2016.02); *A61B 2090/701* (2016.02)

(56) References Cited

FOREIGN PATENT DOCUMENTS

| | | |
|---|---|---|
| JP | H11-151198 A | 6/1999 |
| JP | 2007-202859 A | 8/2007 |
| JP | 2009-240434 A | 10/2009 |
| JP | 3205321 U | 7/2016 |
| WO | WO 2013/021701 A1 | 2/2013 |

* cited by examiner

ENDOSCOPE ACCESSORY CASE

CROSS REFERENCE TO RELATED APPLICATION

This application is a continuation application of PCT/JP2016/075220 filed on Aug. 29, 2016 and claims benefit of Japanese Application No. 2016-065771 filed in Japan on Mar. 29, 2016, the entire contents of which are incorporated herein by this reference.

BACKGROUND OF THE INVENTION

1. Field of the Invention

The present invention relates to an endoscope accessory case.

2. Description of the Related Art

Conventionally, there is an endoscope cleaning/disinfecting apparatus configured to clean and disinfect contaminated endoscopes. In the endoscope cleaning/disinfecting apparatus, a cleaning basket configured to hold accessories is provided in a treatment tank so that accessories taken out of an endoscope can also be cleaned and disinfected together with the endoscope. For example, Japanese Patent Application Laid-Open Publication No. 2009-240434 discloses a cleaning basket formed of a mesh material, configured to hold accessories, and capable of cleaning the accessories using ultrasound radiated to a cleaning fluid in the treatment tank and using the cleaning fluid ejected from a nozzle.

SUMMARY OF THE INVENTION

An endoscope accessory case according to one aspect of the present invention includes: a case body made up of a bottom portion and an impermeable trunk portion, the case body including an opening portion provided in a top face, and a fluid introduction port configured to introduce a fluid; and an impermeable lid, the lid including a contact portion configured to come into contact with the case body, and a bubble lead-out edge located at a position apart from an inner circumference of the case body and configured to lead out bubbles separated from endoscope accessories when the endoscope accessories held in the case body are agitated by being pushed by the fluid, the lid being configured to detachably cover the opening portion.

DETAILED DESCRIPTION OF THE PREFERRED EMBODIMENT

An embodiment of the present invention will be described below with reference to the drawings.

(Configuration)

Figure 1:
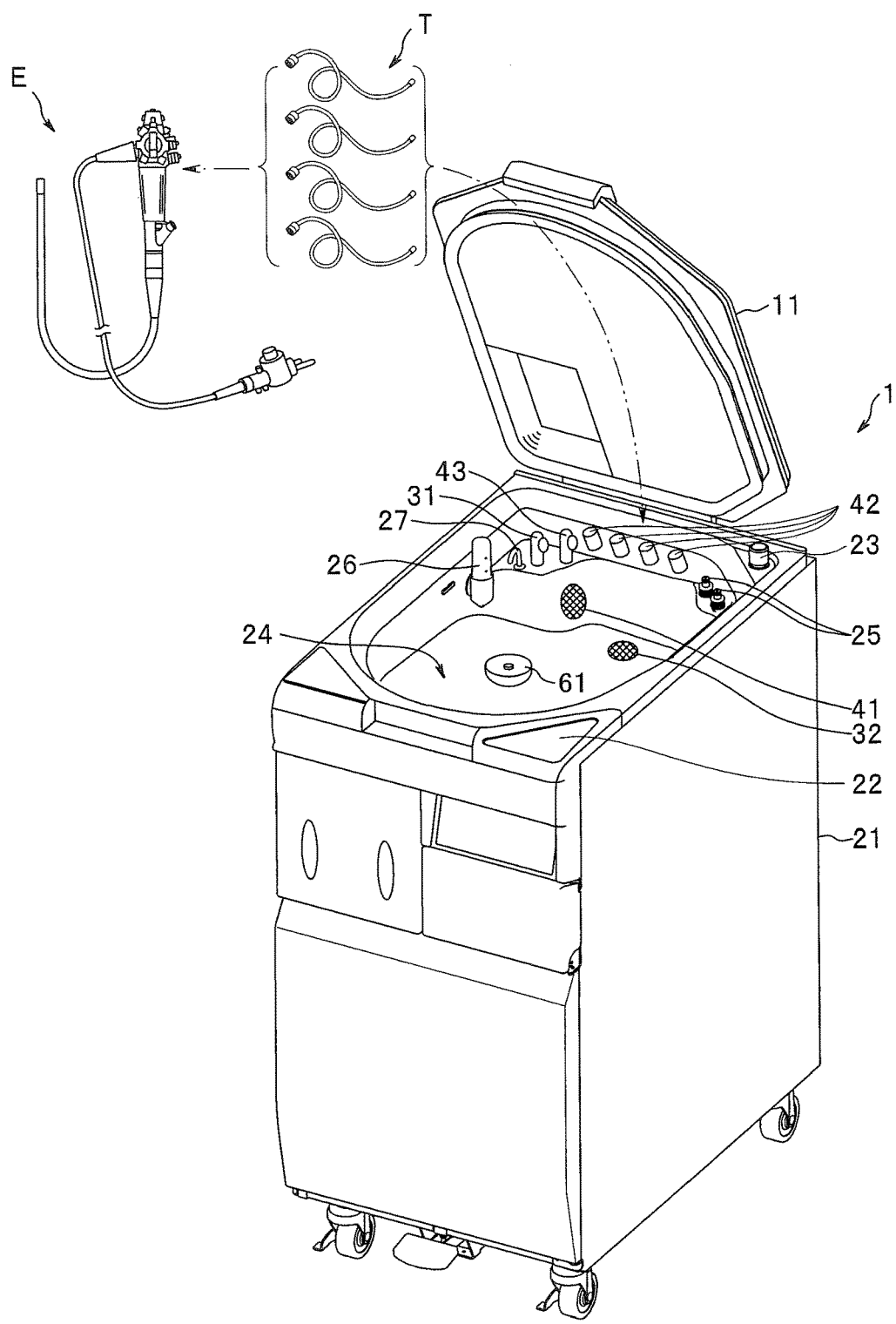
FIG. 1 is an explanatory diagram illustrating an external configuration of an endoscope reprocessor according to an embodiment of the present invention.

FIG. 1 is an explanatory diagram illustrating an external configuration of an endoscope reprocessor 1 according to an embodiment of the present invention. In FIG. 1, a holder net 67 described later is omitted and an endoscope accessory case 61 is represented by an outline shape.

The endoscope reprocessor 1 is an apparatus which performs a reprocessing process of a contaminated endoscope E and parts, accessories, or the like (hereinafter referred to simply as "accessories") A of the endoscope E. The reprocessing process as referred to herein is not particularly limited, and may be any of rinsing using water, cleaning for removing contaminants such as organic matter, disinfecting for neutralizing predetermined microbes, sterilization for eliminating or killing all microbes, or a combination of these processes. The accessories A are not particularly limited, and examples of the accessories A include a suction button attached to the endoscope E before use and removed from the endoscope E before the reprocessing process, an air/water feeding button, and a distal end cover configured to cover a distal end of the endoscope E.

Figure 2:
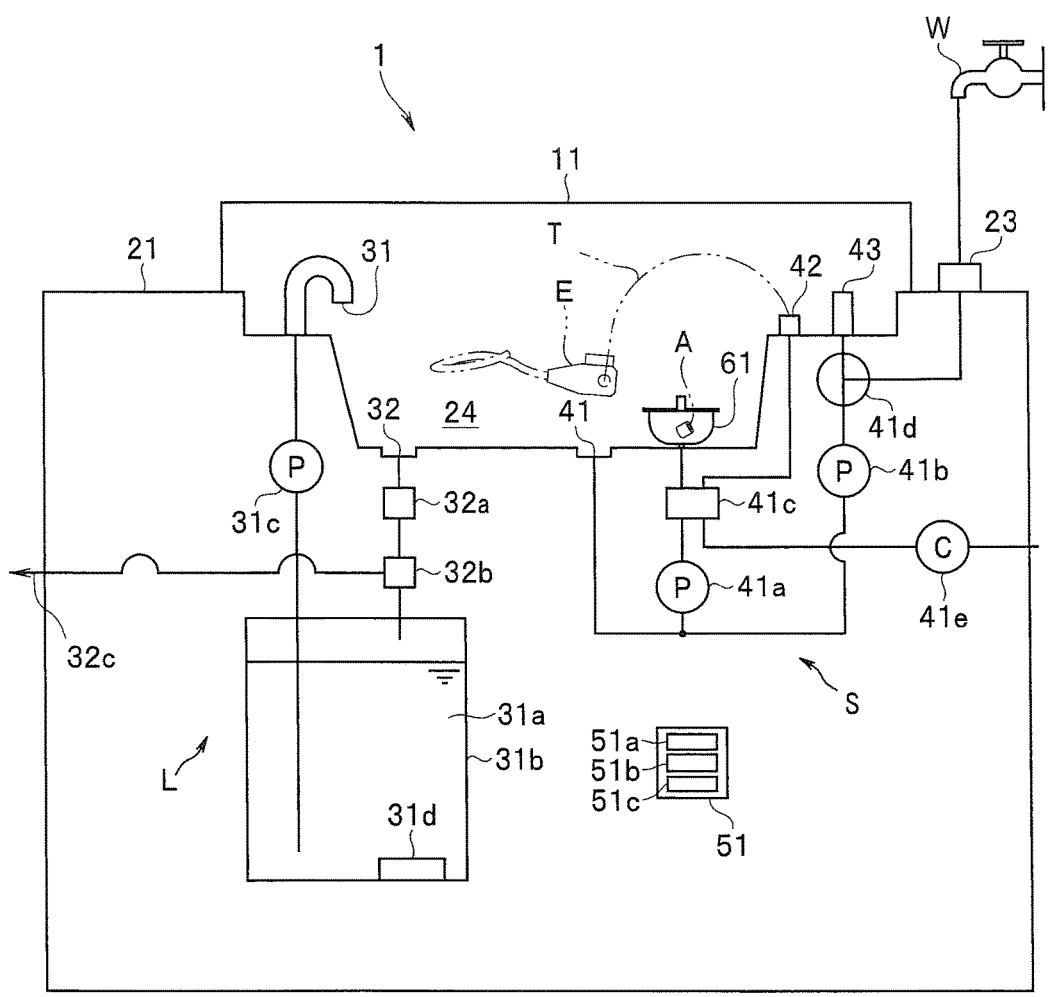
FIG. 2 is an explanatory diagram illustrating a configuration of the endoscope reprocessor according to the embodiment of the present invention.

The endoscope reprocessor 1 includes a top cover 11 and an apparatus body 21. The apparatus body 21 has an operation portion 22 on a front face to accept various user commands concerning the reprocessing process of the endoscope E. The apparatus body 21 is provided with a water supply hose connecting portion 23 and connected to external water supply means W (FIG. 2).

The top cover 11 is provided openably/closably with respect to the treatment tank 24, covering the treatment tank 24, and when the top cover 11 is opened, an inside of the treatment tank 24 is exposed to the outside.

In FIG. 1, the treatment tank 24 is formed in a shape of a tub in which the endoscope E can be placed, but this is not restrictive. The treatment tank 24 includes a leak test port 25, a water level sensor 26, a detergent nozzle 27, a medicinal solution introduction port 31, a drain hole 32, a circulation port 41, a connector 42, a circulation nozzle 43, and the endoscope accessory case 61. The medicinal solution introduction port 31 is connected to a medicinal solution introduction portion L (FIG. 2) described later. The circulation port 41 and circulation nozzle 43 are connected to a fluid feeding portion S (FIG. 2) described later.

The endoscope reprocessor 1 is connected to the endoscope E via a connecting tube T. Note that in FIG. 1, the endoscope reprocessor 1 and endoscope E are connected by four connecting tubes T. However, a direct-connect structure may be used without using any connecting tube T.

After the endoscope E is connected to the endoscope reprocessor 1, the endoscope E is placed in the treatment tank 24, the accessories A are put in the endoscope accessory case 61, and the endoscope E and accessories A are cleaned and disinfected.

Next, a configuration of the endoscope reprocessor 1 will be described.

FIG. 2 is an explanatory diagram illustrating a configuration of the endoscope reprocessor 1 according to the embodiment of the present invention. In FIG. 2, conduits are indicated by solid lines and electrical signal lines are omitted.

The endoscope reprocessor 1 includes the medicinal solution introduction portion L, the drain hole 32, the fluid feeding portion S, the endoscope accessory case 61, and a control unit 51.

The medicinal solution introduction portion L is configured to be able to supply a medicinal solution 31a such as an antiseptic solution to the treatment tank 24. The medicinal solution introduction portion L includes a medicinal solution tank 31b and a medicinal solution pump 31c.

The medicinal solution tank 31b can accumulate the medicinal solution 31a. The medicinal solution tank 31b is connected to the medicinal solution introduction port 31. The medicinal solution tank 31b includes a warming unit 31d connected to the control unit 51 and can warm the medicinal solution 31a in the medicinal solution tank 31b under control of the control unit 51.

The medicinal solution pump 31c is a pump used to feed the solution from the medicinal solution tank 31b to the treatment tank 24. The medicinal solution pump 31c is disposed in a conduit between the medicinal solution tank 31b and medicinal solution introduction port 31. The medicinal solution pump 31c is connected to the control unit 51, and is capable of taking in the medicinal solution 31a from the medicinal solution tank 31b and feeding the medicinal solution 31a to the treatment tank 24 through the medicinal solution introduction port 31 under the control of the control unit 51.

The drain hole 32 is configured to be able to drain the liquid accumulated in the treatment tank 24. The drain hole 32 can be communicated with either of the medicinal solution tank 31b and external drainage means 32c through an on-off valve 32a and three-way valve 32b. The on-off valve 32a is made up of a solenoid valve connected to the control unit 51 and is capable of communicating the drain hole 32 with a conduit connected to the three-way valve 32b, under the control of the control unit 51. The three-way valve 32b is made up of a direction selector valve connected to the control unit 51 and is capable of communicating the drain hole 32, which is communicated with the three-way valve 32b through the on-off valve 32a, with either of the medicinal solution tank 31b and external drainage means 32c under the control of the control unit 51.

The fluid feeding portion S is configured to be able to feed air or a liquid to the connector 42, circulation nozzle 43, and endoscope accessory case 61. For example, the fluid feeding portion S includes a liquid feeding pump 41a, a circulating pump 41b, a flow path selector valve 41c, a water supply selector valve 41d, and an air compressor 41e.

The liquid feeding pump 41a is a pump used to feed the liquid in the treatment tank 24 to the connector 42 and endoscope accessory case 61. The liquid feeding pump 41a is disposed in a conduit between the circulation port 41 and flow path selector valve 41c. The liquid feeding pump 41a can be communicated with either of the connector 42 and endoscope accessory case 61 through the flow path selector valve 41c. The liquid feeding pump 41a is connected to the control unit 51 and is capable of taking in the liquid from the treatment tank 24 through the circulation port 41 and feeding the liquid to a conduit connected to the flow path selector valve 41c, under the control of the control unit 51.

The flow path selector valve 41c is made up of a direction selector valve connected to the control unit 51. The flow path selector valve 41c is connected to the liquid feeding pump 41a, air compressor 41e, connector 42, and endoscope accessory case 61 and configured to communicate at least one of the liquid feeding pump 41a and air compressor 41e with at least one of the connector 42 and endoscope accessory case 61 under the control of the control unit 51.

The circulating pump 41b is a pump used to feed the liquid from the treatment tank 24 to the circulation nozzle 43. The circulating pump 41b is disposed in a conduit between the circulation port 41 and circulation nozzle 43. The circulating pump 41b is connected to the control unit 51 and configured to take in the liquid through the circulation port 41 and feed the liquid to the circulation nozzle 43 under the control of the control unit 51.

The water supply selector valve 41d is made up of a direction selector valve connected to the control unit 51. The water supply selector valve 41d is connected to the circulation nozzle 43, circulating pump 41b, and water supply hose connecting portion 23, and configured to communicate the circulation nozzle 43 with either the circulating pump 41b or external water supply means under the control of the control unit 51.

The air compressor 41e is a pump used to feed outside air to the connector 42 and endoscope accessory case 61. The air compressor 41e is open to outside air and is communicated with the flow path selector valve 41c. The air compressor 41e is connected to the control unit 51 and configured to take in air from outside and feed the air to a conduit connected to the flow path selector valve 41c, under the control of the control unit 51.

The control unit 51 includes a central processing unit (hereinafter referred to as a "CPU") 51a, a ROM 51b, and a RAM 51c. The CPU 51a can read and execute various programs stored in the ROM 51b and RAM 51c.

The ROM 51b stores various programs related to the reprocessing process of the endoscope E.

Functions of the control unit 51 are implemented when the CPU 51a executes various programs stored in the ROM 51b.

Figure 3:
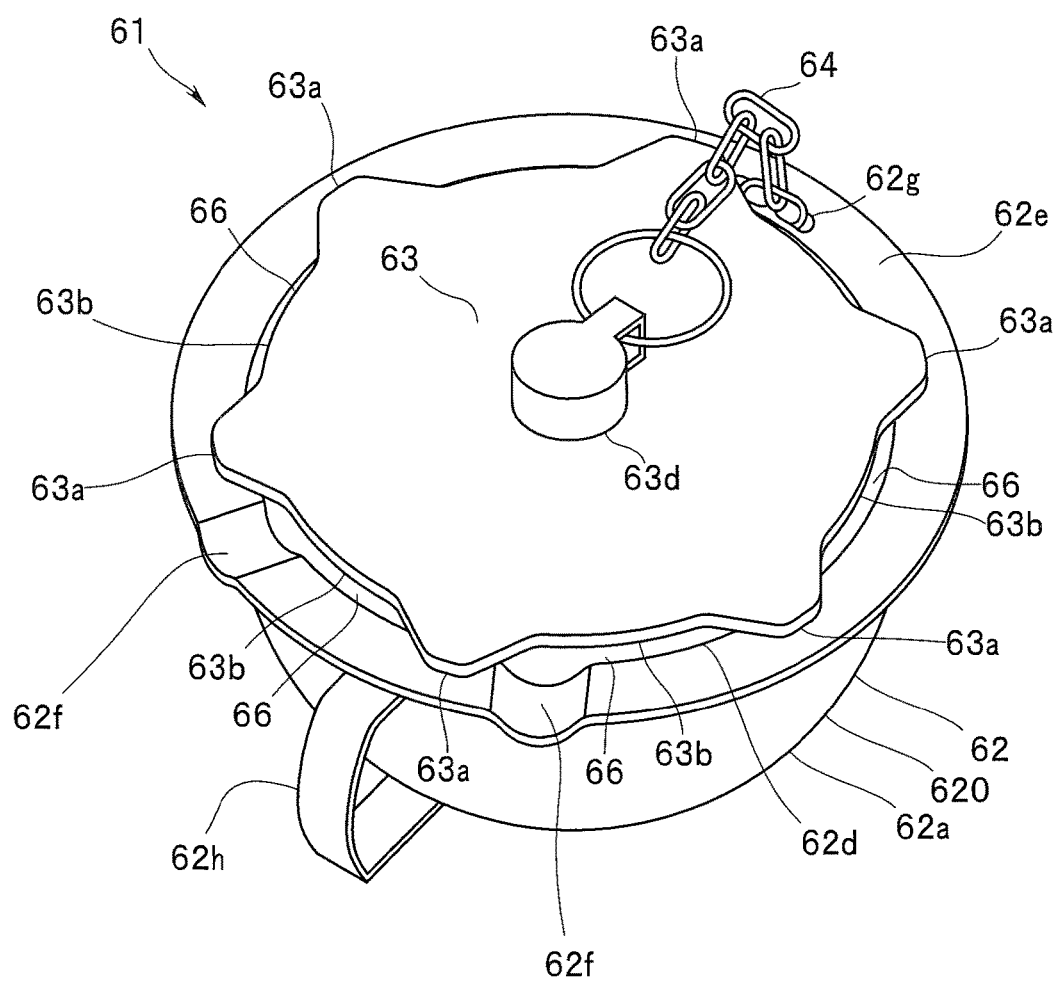
FIG. 3 is a perspective view of an endoscope accessory case for the endoscope reprocessor according to the embodiment of the present invention.
Figure 4:
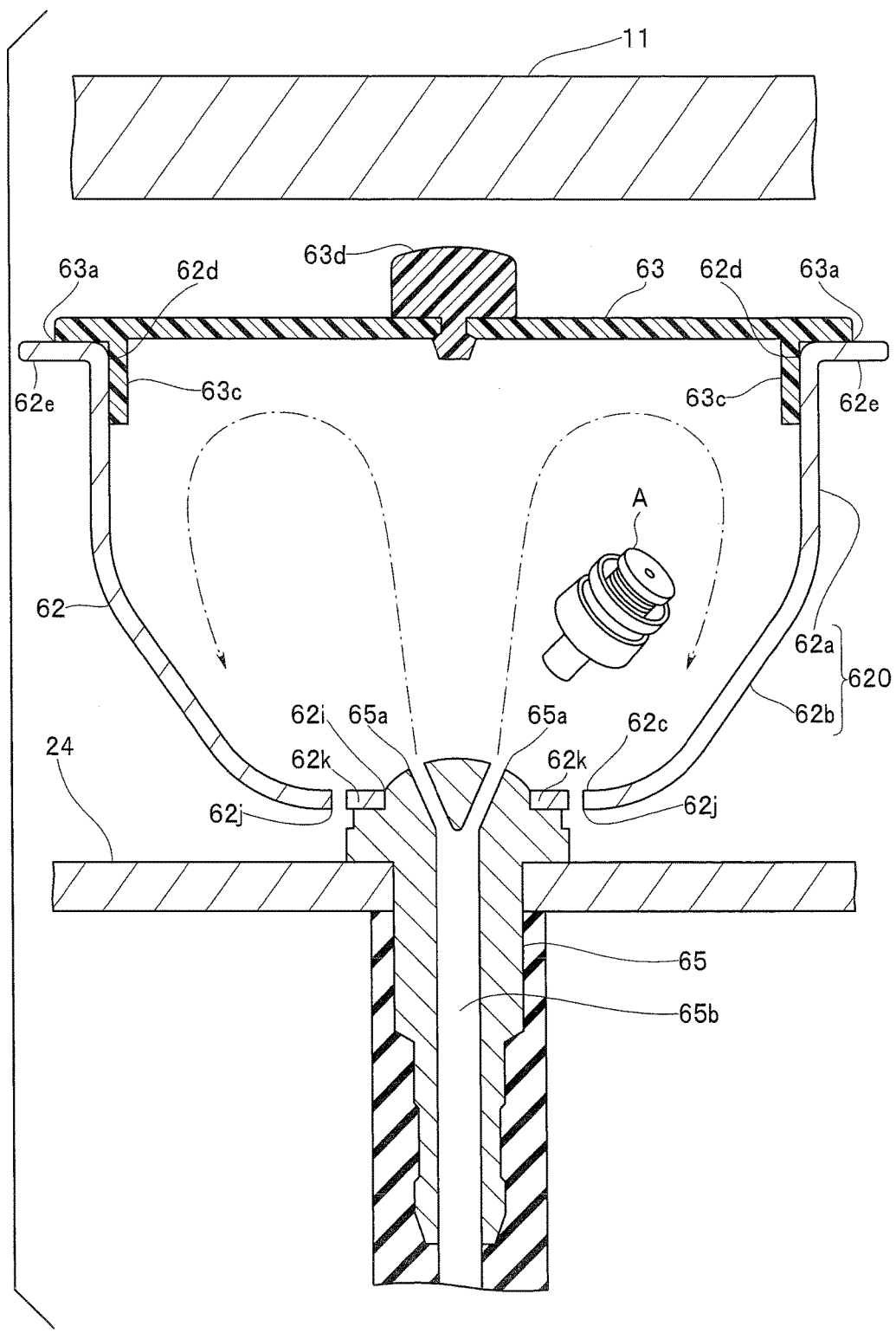
FIG. 4 is a cut end view of the endoscope accessory case and a nozzle for the endoscope reprocessor according to the embodiment of the present invention.
Figure 5:
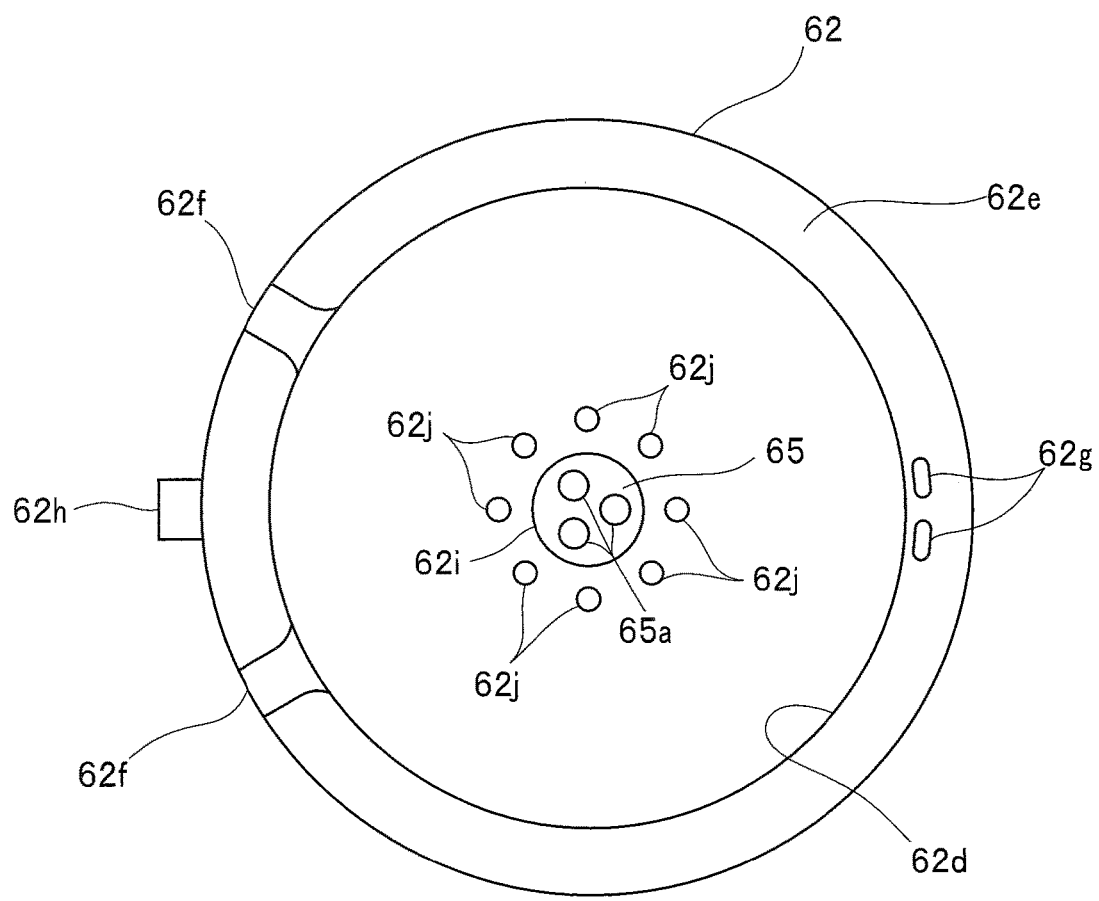
FIG. 5 is a top view of a case body of the endoscope accessory case and the nozzle for the endoscope reprocessor according to the embodiment of the present invention.
Figure 6:
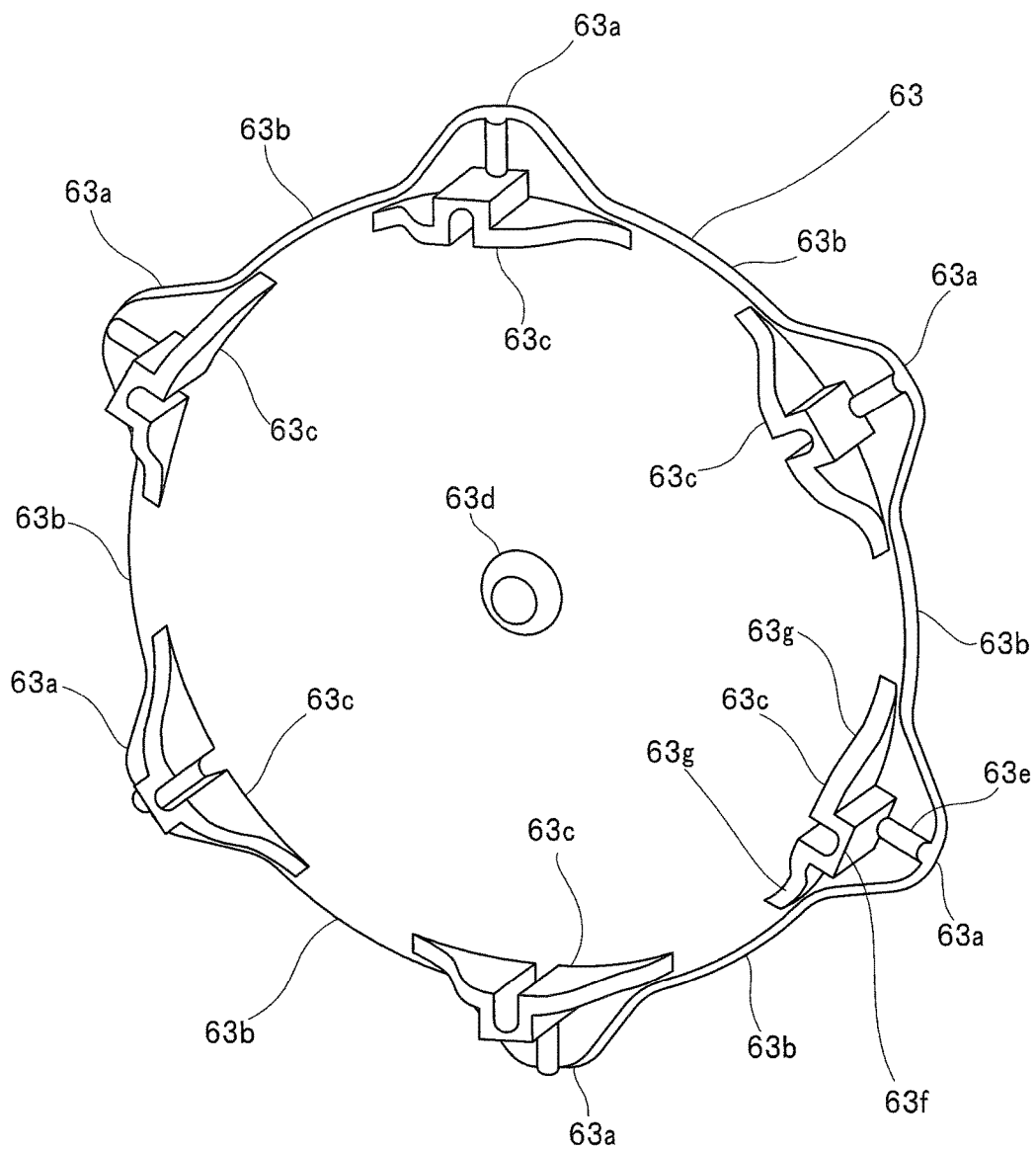
FIG. 6 is a perspective view showing an undersurface of a lid of the endoscope accessory case for the endoscope reprocessor according to the embodiment of the present invention.

FIG. 3 is a perspective view of the endoscope accessory case 61 for the endoscope reprocessor 1 according to the embodiment of the present invention. FIG. 4 is a cut end view of the endoscope accessory case 61 and a nozzle 65 for the endoscope reprocessor 1 according to the embodiment of the present invention. FIG. 5 is a top view of a case body 62 of the endoscope accessory case 61 and the nozzle 65 for the endoscope reprocessor 1 according to the embodiment of the present invention. FIG. 6 is a perspective view showing an undersurface of a lid 63 of the endoscope accessory case 61 for the endoscope reprocessor 1 according to the embodiment of the present invention.

The endoscope accessory case 61 is configured to be able to hold the accessories A. The endoscope accessory case 61 includes the case body 62 and the lid 63. The case body 62 and lid 63 are coupled together by a coupler 64 made up, for example, of a chain. The endoscope accessory case 61 is attached to the nozzle 65 provided in the treatment tank 24.

The case body 62 is configured to be able to hold the accessories A inside. Of the case body 62, at least a trunk portion 620 is configured, for example, to be impermeable. Being impermeable as referred to herein indicates a structure, such as a solid plate, which does not allow passage of a fluid, and is distinguished from a structure, such as a mesh structure, which allows passage of a fluid. Material of the case body 62 is not particularly limited, but metal, resin, or ceramics can be used, for example.

The case body 62 is not particularly limited in shape, but the case body 62 is formed, for example, into a bowl shape, a tubular shape, a semispherical shape, or a tapered shape. The case body 62 includes the trunk portion 620 and a bottom portion 62c. Depending on the shape of the case body 62, the trunk portion 620 may be made up of an upper trunk portion 62a and a lower trunk portion 62b.

The upper trunk portion 62a is formed into a tubular shape and provided with an opening portion 62d in a top face. A ring-shaped outward flange 62e is formed around the opening portion 62d. Two continuous recess portions 62f are formed on the outward flange 62e, running through the outward flange 62e from an inner edge to an outer edge of the outward flange 62e. A coupler mounting hole 62g is formed in the outward flange 62e. The coupler 64 for use to couple to the lid 63 is mounted in the coupler mounting hole 62g. A convex portion 62h for use to set the upper trunk portion 62a in a positioning portion 67a of the holder net 67 described later is provided on an outer circumference of the upper trunk portion 62a. The lower trunk portion 62b is not particularly limited, but if the lower trunk portion 62b is formed so as to narrow toward a center, for example, it becomes easier for the introduced fluid to circulate, and for the held accessories A to be agitated.

The bottom portion 62c is provided, extending toward a center from the lower trunk portion 62b. The bottom portion 62c includes a fluid introduction port 62i for use to introduce the fluid to the center. The bottom portion 62c includes a fixing portion 62k for use to fix the bottom portion 62c to the nozzle 65.

However, a placement location of the fluid introduction port 62i is not limited to the bottom portion 62c, and the fluid introduction port 62i may be provided in the trunk portion 620.

Also, the case body 62 may be structured to be supplied with the fluid from the connector 42 rather than from the nozzle 65 provided in the treatment tank 24 of the endoscope reprocessor 1. In that case, preferably the case body 62 is provided with a tube connecting portion communicated with the fluid introduction port 62i and connected to the connecting tube T.

A fluid lead-out hole 62j may be formed in the bottom portion 62c. The number of fluid lead-out holes 62j is not particularly limited, and one or more fluid lead-out holes is sufficient. Once the fluid lead-out hole 62j is disposed, the liquid accumulated in the treatment tank 24 can be drained through the fluid lead-out hole 62j, allowing the case body 62 to be dried.

The lid 63 is configured to be able to detachably cover the opening portion 62d of the case body 62. The lid 63 is made, for example, of metal, ceramics, or resin and is configured to be impermeable. The lid 63 includes a contact portion 63a, a bubble lead-out edge 63b, a protruding portion 63c, and a knob 63d.

Note that whereas six each of contact portions 63a, bubble lead-out edges 63b, protruding portions 63c, and bubble lead-out ports 66 are shown in FIGS. 3 and 6, the contact portion 63a, bubble lead-out edge 63b, protruding portion 63c, and bubble lead-out port 66 as referred to herein indicate any one of or six of the contact portions 63a, bubble lead-out edges 63b, protruding portions 63c, and bubble lead-out ports 66, respectively.

Six contact portions 63a are provided at equal intervals on an outer circumference of the lid 63 in such a way as to contact the outward flange 62e of the case body 62. The contact portions 63a are formed on the outer circumference of the lid 63, protruding outward in the form of tongues. Each of the contact portions 63a has a rib 63e at a center of an undersurface (FIG. 6).

Six bubble lead-out edges 63b are provided at equal intervals on the outer circumference of the lid 63. The bubble lead-out edges 63b are disposed inward of an edge of the opening portion 62d such that gaps will be formed between the bubble lead-out edges 63b and the edge of the opening portion 62d of the case body 62.

More specifically, the protruding portions 63c are formed in a region linking the center of the lid 63 and the contact portions 63a and formed protruding toward the bottom portion 62c of the case body 62 from a circumferential edge of the undersurface of the lid 63. The number of protruding portions 63c is not particularly limited, and in FIG. 6, six protruding portions 63c are provided at equal intervals at proximal ends of the contact portions 63a. The protruding portion 63c has a central portion 63f and left and right portions 63g (FIG. 6). The central portion 63f is formed convexly toward the outer circumference of the lid 63 in such a way as to hit an inner circumference of the case body 62. The left and right portions 63g are respectively formed on left and right sides of the central portion 63f in such a way that a projection height from the lid 63 will be reduced gradually toward both left and right ends of the protruding portion 63c from the side of the central portion 63f. The six protruding portions 63c are configured to be able to be fitted in the case body 62.

That is, the lid 63 includes the contact portions 63a configured to contact the case body 62 and the bubble lead-out edges 63b disposed at positions spaced away from the inner circumference of the case body 62 and used to lead out bubbles and is configured to be able to detachably cover the opening portion 62d.

When the lid 63 is attached to the case body 62, the bubble lead-out ports 66 are formed by the edge of the opening portion 62d of the case body 62 and the bubble lead-out edges 63b of the lid 63. The bubble lead-out ports 66 are disposed on a circumferential edge of the opening portion 62d.

The knob 63d is attached to a center of the lid 63. The coupler 64 for use to couple to the case body 62 is attached to the knob 63d.

The nozzle 65 is disposed on the bottom portion 62c of the case body 62 and is configured to be able to introduce the fluid into the case body 62. The nozzle 65 includes a jet nozzle 65a (FIG. 5) configured to emit a jet of fluid and a fluid flow path 65b communicated with the jet nozzle 65a. The number of jet nozzles 65a is not particularly limited, and one or more jet nozzles are sufficient. The fluid flow path 65b is communicated with a conduit connected to the flow path selector valve 41c.

Next, description will be given of how the endoscope accessory case 61 according to the embodiment is set in the treatment tank 24.

Figure 7:
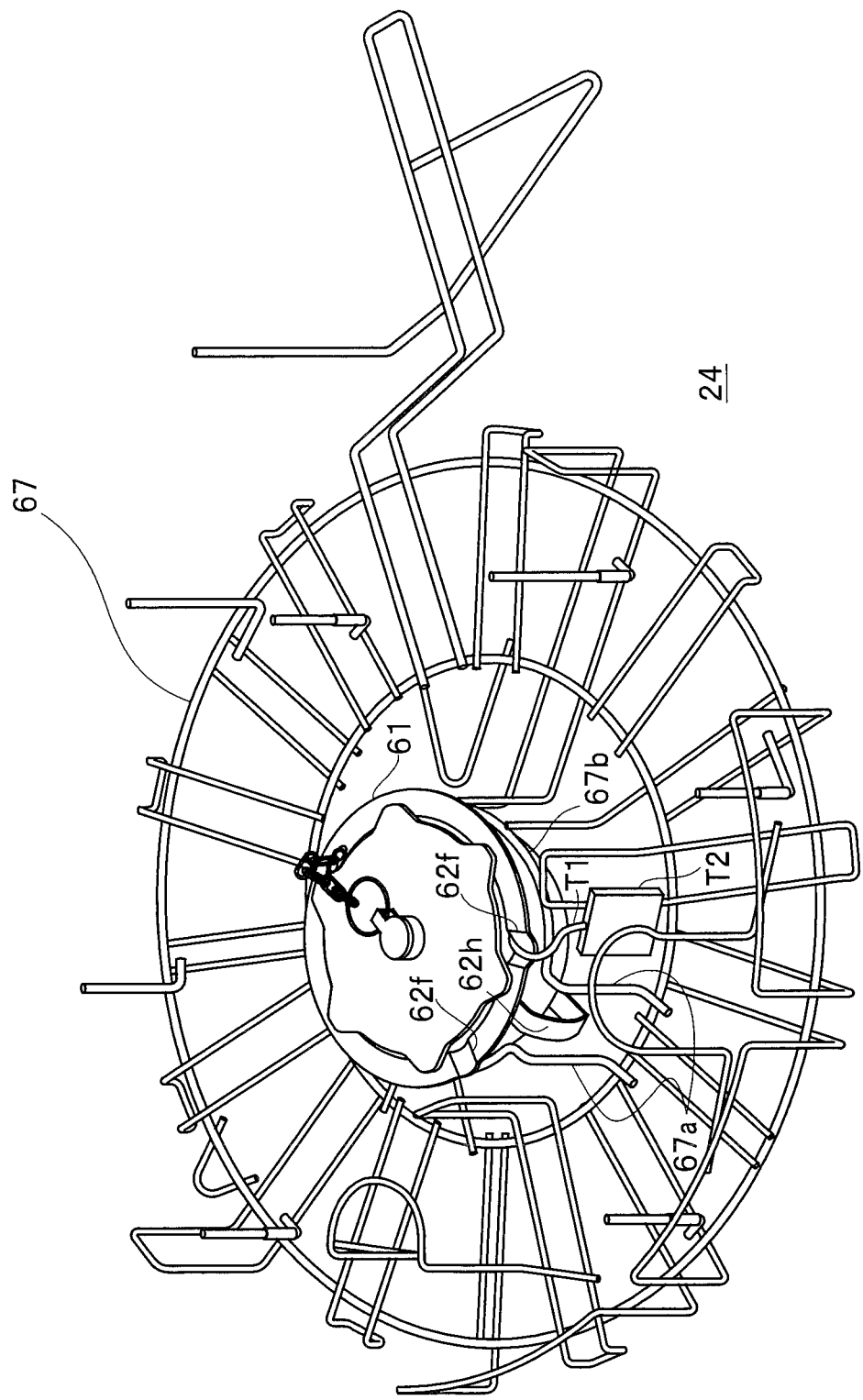
FIG. 7 is an explanatory diagram illustrating how the endoscope accessory case for the endoscope reprocessor according to the embodiment of the present invention is set in a holder net.

FIG. 7 is an explanatory diagram illustrating how the endoscope accessory case 61 for the endoscope reprocessor 1 according to the embodiment of the present invention is set in the holder net 67.

As shown in FIG. 7, the endoscope accessory case 61 is held by the holder net 67 placed in the treatment tank 24. The holder net 67 is made of such a material as metal. The holder net 67 is made of rod-shaped members and includes the positioning portion 67a and a case holding portion 67b.

The endoscope accessory case 61 is placed in the case holding portion 67b such that the convex portion 62h will fit in the positioning portion 67a. If a tag T2 is attached to the accessories A via a chain T1, the chain T1 is drawn out through a continuous recess portion 62f and the tag T2 is placed outside the endoscope accessory case 61 to make it easier to agitate the accessories A.

(Operation)

Next, operation of the endoscope reprocessor 1 and endoscope accessory case 61 according to the embodiment will be described.

An operator opens the top cover 11 and sets the endoscope E on the holder net 67 of the treatment tank 24.

The operator opens the lid 63 of the endoscope accessory case 61, puts the accessories A in the endoscope accessory case 61, and closes the lid 63.

The operator closes the top cover 11. When closed, the top cover 11 hits a top of the knob 63d or is placed at a position a predetermined distance away from the top of the knob 63d. The lid 63 is kept from coming off the case body 62 by the top cover 11.

When a user command to start a reprocessing process is inputted via the operation portion 22, the control unit 51 causes a liquid such as the medicinal solution 31a or water to be poured into the treatment tank 24 through the detergent nozzle 27, medicinal solution introduction port 31, or circulation port 41 and causes the liquid to be accumulated in the treatment tank 24.

When the liquid is accumulated in the treatment tank 24, the endoscope accessory case 61 is submerged, and an inside of the endoscope accessory case 61 is filled with liquid.

When the control unit 51 transmits a control signal, instructing the flow path selector valve 41c to communicate the liquid feeding pump 41a and endoscope accessory case 61 with each other, the liquid feeding pump 41a and endoscope accessory case 61 are communicated with each other. Next, when the control unit 51 transmits a control signal, instructing the liquid feeding pump 41a to start feeding the liquid, the liquid feeding pump 41a starts feeding the liquid. Consequently, the liquid taken in through the circulation port 41 flows into the nozzle 65 through the flow path selector valve 41c and is introduced into the endoscope accessory case 61 through each of the jet nozzles 65a. Note that the control unit 51 may cause the air to be fed into the endoscope accessory case 61 by causing the flow path selector valve 41c to communicate the endoscope accessory case 61 and air compressor 41e with each other or may send both the liquid and gas simultaneously into the endoscope accessory case 61.

The fluid introduced through the jet nozzles 65a flows toward the lid 63 and after being blocked by the lid 63 and protruding portions 63c, passes through the upper trunk portion 62a and lower trunk portion 62b along a wall of the case body 62 and flows to the bottom portion 62c (alternate long and short dashed lines in FIG. 4). The accessories A are agitated by being pushed by the fluid flowing in the endoscope accessory case 61. Being agitated and hitting the lower trunk portion 62b, the accessories A are brought toward the bottom portion 62c along the lower trunk portion 62b. The bubbles adhering to the accessories A are separated from the accessories A and led out together with part of the fluid through the bubble lead-out ports 66. Part of the fluid is led out through the fluid lead-out hole 62j.

Consequently, the fluid introduced through the jet nozzles 65a is blocked from flowing out by the impermeable case body 62 and lid 63 and thereby flows strongly within the endoscope accessory case 61, agitating and cleaning/disinfecting the accessories A.

According to the embodiment described above, the endoscope accessory case 61 can agitate the accessories A effectively.

Note that although in the embodiment, six each of the contact portions 63a, bubble lead-out edges 63b, and protruding portions 63c are disposed at equal intervals on the outer circumference of the lid 63, the present invention is not limited to an equidistant arrangement or a group of six.

Note that although in the embodiment, each of the contact portions 63a has the rib 63e at a center on an underside, the contact portion 63a may not have the rib 63e.

Note that although in the embodiment, each of the protruding portions 63c includes the central portion 63f and the left and right portions 63g, the present invention is not limited to a configuration made up of the central portion 63f and the left and right portions 63g. The protruding portion 63c may be formed, for example, into a block shape, plate shape, or columnar shape, extending from the proximal end of the contact portion 63a to the bottom portion 62c of the case body 62.

Note that although an example in which the air compressor 41e can be communicated with the endoscope accessory case 61 is shown in FIG. 2, the present invention is not limited to this, and may be configured to allow only the liquid to be introduced into the endoscope accessory case 61.

The present invention is not limited to the embodiment described above, and various changes, alterations and the like are possible without departing from the spirit of the invention.

The present invention can provide an endoscope accessory case which can effectively agitate accessories.

What is claimed is:

1. An endoscope accessory case comprising:
a case body comprising an opening formed in a top face, a ring-shaped outward flange formed around the opening, a fluid introduction port configured to introduce a fluid, an impermeable trunk, and a bottom provided at a lower part of the trunk; and
an impermeable lid comprising an outer circumference, the outer circumference comprising a contact portion protruding in a tongue shape and a bubble lead-out edge, the lid being formed to be attachable to and detachable from the opening, wherein
when the lid is attached to the opening, the outward flange and the contact portion come into contact with each other, the bubble lead-out edge is located at a position apart from an inner circumference of the case body, and a gap is created between an edge of the opening and the bubble lead-out edge, the gap forming a bubble lead-out port configured to lead out bubbles separated from endoscope accessories when the endoscope accessories held in the case body are agitated by being pushed by the fluid.

2. The endoscope accessory case according to claim 1, wherein the fluid introduction port is disposed on the bottom of the case body.

3. The endoscope accessory case according to claim 1, further comprising a fixing portion fixed to an endoscope reprocessor.

4. The endoscope accessory case according to claim 1, further comprising a protruding portion formed in a region linking a center of the lid and the contact portion and formed protruding toward the bottom of the case body from an undersurface of the lid.

5. The endoscope accessory case according to claim 4, wherein the protruding portion is configured to hit an inner circumference of the case body.

* * * * *